(12) United States Patent
Mirza et al.

(10) Patent No.: US 11,051,848 B2
(45) Date of Patent: Jul. 6, 2021

(54) CANNULA FOR A SURGICAL INSTRUMENT

(71) Applicant: A.M. SURGICAL, INC., Smithtown, NY (US)

(72) Inventors: Romi Mirza, Smithtown, NY (US); Ather Mirza, Smithtown, NY (US)

(73) Assignee: A.M. Surgical, Inc., Smithtown, NY (US)

( * ) Notice: Subject to any disclaimer, the term of this patent is extended or adjusted under 35 U.S.C. 154(b) by 108 days.

(21) Appl. No.: 16/173,824

(22) Filed: Oct. 29, 2018

(65) Prior Publication Data

US 2019/0059943 A1 Feb. 28, 2019

Related U.S. Application Data

(63) Continuation of application No. 15/243,674, filed on Aug. 22, 2016, now Pat. No. 10,201,372.

(51) Int. Cl.
| | |
|---|---|
| *A61B 17/34* | (2006.01) |
| *A61B 17/32* | (2006.01) |
| *A61B 1/04* | (2006.01) |
| *A61B 17/00* | (2006.01) |
| *A61B 90/00* | (2016.01) |

(52) U.S. Cl.
CPC ........... *A61B 17/3423* (2013.01); *A61B 1/04* (2013.01); *A61B 17/00234* (2013.01); *A61B 17/320016* (2013.01); *A61B 17/320036* (2013.01); *A61B 17/3421* (2013.01); *A61B 17/3496* (2013.01); *A61B 90/361* (2016.02); *A61B 2017/00902* (2013.01); *A61B 2017/00907* (2013.01); *A61B 2017/3445* (2013.01); *A61B 2017/3454* (2013.01)

(58) Field of Classification Search
CPC ................... A61B 17/3423; A61B 17/320036
See application file for complete search history.

(56) References Cited

U.S. PATENT DOCUMENTS

| | | | |
|---|---|---|---|
| 4,926,770 A | 5/1990 | Hanyu et al. | |
| 4,963,147 A | 10/1990 | Agee et al. | |
| 5,089,000 A | 2/1992 | Agee et al. | |
| 5,306,284 A | 4/1994 | Agee et al. | |
| 5,569,283 A * | 10/1996 | Green | A61B 17/320036 30/162 |
| 5,848,978 A * | 12/1998 | Cecchi | A61B 10/0266 600/567 |
| 7,628,798 B1 | 12/2009 | Welborn | |
| 2007/0123889 A1* | 5/2007 | Malandain | A61B 17/320016 606/79 |
| 2010/0228275 A1 | 9/2010 | Welborn | |
| 2014/0066709 A1 | 3/2014 | Mirza et al. | |
| 2014/0371526 A1 | 12/2014 | Mirza et al. | |
| 2016/0235431 A1* | 8/2016 | Brown | A61B 17/3421 |

OTHER PUBLICATIONS

U.S. Appl. No. 15/243,674, filed Aug. 22, 2016, Pending.
U.S. Appl. No. 16/173,824, filed Oct. 29, 2018, Pending.

* cited by examiner

*Primary Examiner* — Andrew Yang
(74) *Attorney, Agent, or Firm* — Bodner & O'Rourke, LLP; Gerald T. Bodner; Christian P. Bodner

(57) ABSTRACT

This disclosure relates to a cannula for a surgical instrument used for cutting selected tissue in a body cavity while under visual inspection. A kit containing the cannula and methods for performing surgical procedures using the cannula are also described.

14 Claims, 1 Drawing Sheet

CANNULA FOR A SURGICAL INSTRUMENT

This application is a Continuation of U.S. application Ser. No. 15/243,674, filed Aug. 22, 2016. The entirety of the aforementioned applications is incorporated herein by reference.

FIELD

This application generally relates to medical devices. In particular, the application relates to surgical instruments and the use thereof.

BACKGROUND

Conventional surgical techniques and equipment often require a fairly large incision over the surgical site and spreading of the incision to allow viewing and instrument access. These techniques can require a longer period of recovery than endoscopic methods and have greater levels of post-operative pain due to the incision size and level of manipulation during the procedure.

Endoscopic and arthroscopic surgeries are minimally invasive surgical procedures that are performed through small incisions or natural body openings. An endoscopic or arthroscopic procedure typically involves use of specialized devices and direct- or remote-control manipulation of instruments with indirect observation of the surgical field through an endoscope, arthroscope or similar device. Compared to open surgery, endoscopic and arthroscopic surgery is a minimally invasive surgery with less postoperative pain, early resumption of usual activities and a cosmetically appealing scar. It typically results in shorter hospital stays, or allows outpatient treatment.

In general, arthroscopy is applied to introduction of a scope into a joint anywhere in the body. Arthroscopic surgery refers to the process of introducing of the instrument to, and performing an operation at the joint. Endoscopy is applied to introduction of a scope into a body cavity anywhere in the body. Endoscopic surgery refers to the process of introducing the instruments and performing surgery at the operation site. Further nomenclature is designated by the anatomical structure the scope is introduced into, for example if the scope is placed in the stomach it is called Gastroscopy, in the abdomen it is Laprascopy, etc. There are places where no actual cavity exists. Here, surgeons can create a cavity by introducing a slotted cannula to visualize the surroundings without soft tissue obstruction, as in endoscopic carpal tunnel and cubital tunnel.

As seen in recent outbreaks of infections in hospitals, the insufficient or improper sterilization of re-usable surgical implements, can result in the introduction of microorganisms, including drug-resistant bacteria, into the patient, potentially resulting in severe, or even lethal, infections. This risk is magnified in procedures that require the insertion of multiple instruments into an incision.

The present application fulfills a need in the art for a disposable cannula attachable to endoscopic and arthroscopic surgical instruments useful in uniportal procedures. Additionally, the present application provides a clear cannula that allows visual observation of all tissues around the cannula, reducing the risk dividing unintended structures.

SUMMARY

One aspect of the present invention relates to a cannula for a surgical instrument used for cutting selected tissue in a body cavity while under visual inspection. The cannula comprises a hollow central lumen extending from its proximal end to its distal end; the proximal end being open and connectable to a surgical handpiece, allowing passage of an optical system and a cutting tool extension system into said hollow central lumen; and said distal end being closed. The cannula has a flat top surface with a lateral slot in the proximity of said distal end through which a cutting blade can be extended and retracted under operation of the cutting tool extension system while visualizing tissue at said lateral slot with said optical system. The flat top surface has a width dimension spanning a distance from a first side to a second side of said flat top surface. The cannula further has a contiguous lower surface having the lateral sides thereof connected to said first side and said second side of said flat top surface, said lower surface being sized to permit a passage of an optical system and a cutting tool extension system between said flat top surface and said lower surface, said lower surface being circular in cross-section, wherein the lateral sides of said lower surface are curved such that they have a maximum width between the lateral sides that is greater than said width dimension of said flat top surface.

Another aspect of the present application relates to a cannula for a surgical instrument used for cutting selected tissue in a body cavity while under visual inspection. The cannula comprises a hollow central lumen extending from its proximal end to its distal end; the proximal end being open and connectable to a surgical handpiece, allowing passage of an optical system and a cutting tool extension system into said hollow central lumen; and said distal end being closed. The cannula is circular in cross-section and has a lateral slot in the proximity of said distal end through which a cutting blade can be extended and retracted under operation of the cutting tool extension system while visualizing tissue at said lateral slot with said optical system.

Another aspect of the present application relates to an instrument kit for implementing an endoscopic or arthroscopic surgical procedure. The kit comprises the cannula of the present application.

Another aspect of the present application relates to a method for performing a uniportal procedure with a cannula for a surgical instrument used for cutting selected tissue in a body cavity while under visual inspection. The cannula comprises a hollow central lumen extending from its proximal end to its distal end; the proximal end being open and connectable to a surgical handpiece, allowing passage of an optical system and a cutting tool extension system into said hollow central lumen; and said distal end being closed. The cannula has a flat top surface with a lateral slot in the proximity of said distal end through which a cutting blade can be extended and retracted under operation of the cutting tool extension system while visualizing tissue at said lateral slot with said optical system. The flat top surface has a width dimension spanning a distance from a first side to a second side of said flat top surface. The cannula further has a contiguous lower surface having the lateral sides thereof connected to said first side and said second side of said flat top surface, said lower surface being sized to permit a passage of an optical system and a cutting tool extension system between said flat top surface and said lower surface, said lower surface being circular in cross-section, wherein the lateral sides of said lower surface are curved such that they have a maximum width between the lateral sides that is greater than said width dimension of said flat top surface. The method comprising the steps of: a) establishing an entry portal; b) inserting the distal end of the cannula through the entry portal; c) advancing the cannula to create a passage to the target tissue; d) imaging the target tissue with the optical system; e) performing an endoscopic operation at the target tissue; and f) withdrawing the cannula from the entry portal.

Another aspect of the present application relates to a method for performing uniportal endoscopic carpal tunnel release with a cannula for a surgical instrument used for cutting selected tissue in a body cavity while under visual inspection. The cannula comprises a hollow central lumen extending from its proximal end to its distal end; the proximal end being open and connectable to a surgical handpiece, allowing passage of an optical system and a cutting tool extension system into said hollow central lumen; and said distal end being closed. The cannula has a flat top surface with a lateral slot in the proximity of said distal end through which a cutting blade can be extended and retracted under operation of the cutting tool extension system while visualizing tissue at said lateral slot with said optical system. The flat top surface has a width dimension spanning a distance from a first side to a second side of said flat top surface. The cannula further has a contiguous lower surface having the lateral sides thereof connected to said first side and said second side of said flat top surface, said lower surface being sized to permit a passage of an optical system and a cutting tool extension system between said flat top surface and said lower surface, said lower surface being circular in cross-section, wherein the lateral sides of said lower surface are curved such that they have a maximum width between the lateral sides that is greater than said width dimension of said flat top surface. The method comprising the steps of: a) establishing an entry portal proximal or distal of, and proximate to, the transverse carpal ligament; b) inserting the distal end of the cannula through the entry portal; c) advancing the cannula to create a passage to and under the transverse carpal ligament; d) imaging the transverse carpal ligament and tissues surrounding the cannula with the optical system; e) dividing the transverse carpal ligament; and f) withdrawing the cannula from the entry portal.

DETAILED DESCRIPTION

Figure 1:
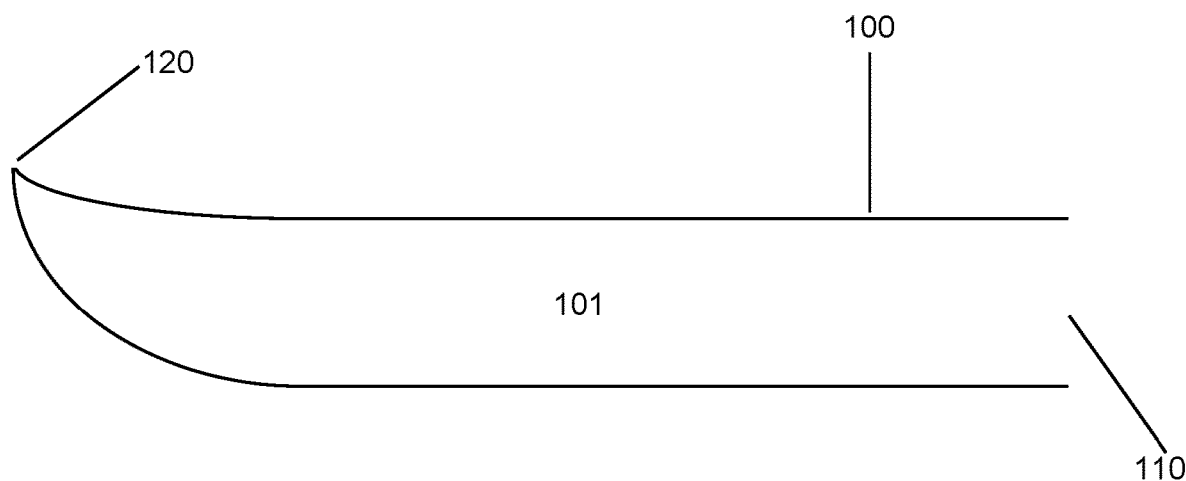
FIG. 1 shows a side view of an exemplary embodiment of the present cannula (not to scale).

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. The present invention is not intended to be limited to the embodiments shown, but is to be accorded the widest possible scope consistent with the principles and features disclosed herein.

This description is intended to be read in connection with the accompanying drawings, which are to be considered part of the entire written description of this application. The drawing figures are not necessarily to scale and certain features of the application may be shown exaggerated in scale or in somewhat schematic form in the interest of clarity and conciseness. In the description, relative terms such as "front," "back," "up," "down," "top," "bottom," "upper," "lower," "distal," and "proximal" as well as derivatives thereof, should be construed to refer to the orientation as then described or as shown in the drawing figure under discussion. These relative terms are for convenience of description and normally are not intended to require a particular orientation. Terms concerning attachments, coupling and the like, such as "connected," "mounted," and "attached," refer to a relationship wherein structures are secured or attached to one another either directly or indirectly through intervening structures, as well as both movable or rigid attachments or relationships, unless expressly described otherwise.

As used herein, the terms "horizontal" and "vertical," and derivatives of those terms, are used in respect to their relationship to the plane defined by the slot in the cannula of the present application. "Vertical" refers to the plane that can, for example, pass through the slot of the cannula and bisect the cannula into two equal halves, while "horizontal" refers to a plane that is perpendicular to the vertical plane. The horizontal plane may be a level plane with respect to the length of the cannula or housing of the device, or may be at an angle to that level plane, allowing some upward or downward movement of elements moving along the horizontal plane with respect to the level plane.

As used herein, the term "subject" refers to an animal. In some embodiments, the animal is a mammal. In further embodiments, the mammal is a human.

As used herein, the term "entry portal" refers to a natural opening or incision in the body of a subject that provides access to a target tissue.

As used herein, the term "uniportal" refers to a procedure in which all instruments that enter the body of the subject are introduced through a single, i.e., the same, entry portal.

The present application provides a cannula for a surgical instrument used for cutting selected tissue in a body cavity while under visual inspection. The surgical instrument may include a surgical handpiece, such as in the carpal tunnel release tool which is described in U.S. Pat. Nos. 4,926,770, 4,963,147, 5,089,000, 5,306,284, and 7,628,798, each of which are herein incorporated by reference.

The use of the present cannula, as attached to a surgical instrument, is exemplified in this application for, but not limited to, endoscopic surgical division of a pulley or tunnel. Some other non-limiting uses for the present cannula, as attached to a surgical instrument, include, for example, other divisions or partial separation of a tendon or ligament, cutting, dividing, separating or making an incision in connective tissue, muscle, cartilage, membranes, skin, other body tissues or organs or any other use of the device that can be envisioned or carried out by the practitioner. As used herein, the term "practitioner" refers to one of skill in the art or any other user of the device. In some embodiments, the device can be used for a uniportal endoscopic viewing and/or surgical procedure. In other embodiments, the device can be used for an arthroscopic, laparoscopic, or thoracoscopic viewing and/or surgical procedure. As used herein, "laparoscopic" and "thoracoscopic" procedures fall within the scope of "endoscopic" and "arthroscopic" procedures.

Endoscopic or arthroscopic surgical procedures that can be performed with a cannula of the present application include, but are not limited to, carpal tunnel release, Guyon's canal (or tunnel) release, cubital tunnel release, plantar fascia release, lateral release for patella realignment, release of radial tunnel, release of pronatar teres, release of trigger finger, release of lacertus fibrosus, tendon release, release of the extensor tendons for lateral epicondylitis, release of medial epicondylitis, release of the posterior and other compartments of the leg, forearm fascia release for fascial compartment syndrome, release of fascial compartments in the upper or lower extremities, relieving the compression of a nerve by a ligament pulley or tunnel, and releasing the travel of a ligament or tendon through a pulley or tunnel. Procedures that can be performed with a cannula or device of the present application include endoscopic or arthroscopic surgical procedures on the spine, such as discectomy for the treatment of degenerative disc disease, herniated discs, bulging discs, pinched nerves or sciatica. Procedures that can be performed with a cannula or device of the present application also include procedures on cranial and facial tissues, as well as fasciotomy release throughout the body. The cannula or device of the present application can be used for blood vessel, including vein or artery, harvesting throughout the body, for example to provide blood vessel graft material in conjunction with a coronary bypass procedure or for a reconstructive surgical procedure. Procedures that can be performed with a cannula or device of the present application also include endoscopic procedures on the wrist and hand, including the palmar and dorsal sides of the hand. Endoscopic procedures that can be performed with a cannula or device of the present application on the hand also include the digits, including the thumb, index finger, middle finger, ring finger and little (pinky) finger. Other examples of endoscopic or arthroscopic procedures that can be performed with a device of the present application include, but are not limited to, observation of internal tissues or injuries, cauterization of vessels, harvesting of tissues for ex vivo growth; obtaining biopsies; spinal surgery; endonasal surgery; mucosal resection; removal of parasites, cysts or tumors, and foreign body retrieval. Still other examples of endoscopic or arthroscopic surgery that can be performed with the device include, but are not limited to, procedures on or within bone, in or around joints or the tendons associated with those joints, as well as any tissue, area or cavity of the body of a subject.

In some embodiments, the present cannula, as attached to a surgical instrument, can be used in the head of a subject. Exemplary procedures in the head include, but are not limited to, nasal surgery, endoscopic sinus surgery, endoscopic pituitary surgery, cranial surgery, endoscopic ear surgery, throat surgery, endodontic surgery and tonsils.

In some embodiments, the present cannula, as attached to a surgical instrument, can be used in the neck of a subject. Exemplary procedures in the neck include, but are not limited to, laryngoscopic surgery, vocal cord surgery, esophageal surgery, thyroid surgery, carotid artery surgery, and brachial plexus surgery.

In some embodiments, the present cannula, as attached to a surgical instrument, can be used in the chest of a subject. Exemplary procedures in the chest include, but are not limited to, endoscopic mediastinal surgery, thoracic surgery, heart surgery, esophageal surgery, and upper gastrointestinal (GI) scoping.

In some embodiments, the present cannula, as attached to a surgical instrument, can be used in a procedure of a finger, hand, foot of a subject.

In some other embodiments, the present cannula, as attached to a surgical instrument, can be used in the abdomen of a subject. Exemplary procedures in the abdomen include, but are not limited to, diagnostic laparoscopy, laparoscopic gastric surgery, laparoscopic liver surgery, laparoscopic pancreatic surgery, laparoscopic nephrectomy and kidney surgery, laparoscopic intestinal surgery, laparoscopic oophorectomy, laparoscopic hysterectomy, laparoscopic urinary bladder surgery, laparoscopic prostate surgery, laparoscopic aortic surgery, laparoscopic appendectomy, laparoscopic colon surgery, endoscopic hysterotomy, endoscopic fetal surgery, endoscopic hernia repair, and endoscopic splenectomy.

In some embodiments, the present cannula, as attached to a surgical instrument, can be used in an upper extremity of a subject. Exemplary procedures in an upper extremity include, but are not limited to, ECTR, ECUTR, endoscopic pronator teres release, forearm fascial compartment release, endoscopic repair of biceps tendon, endoscopic release of lateral and medial epicondylitis, endoscopic release of radial tunnel syndrome, endoscopic surgery of the brachial plexus, endoscopic harvesting of nerve graft, arthroscopy and surgery of wrist, arthroscopy of elbow, arthroscopy and surgery of the carpometacarpal (CMC) joint, arthroscopy and surgery of shoulder, arthroscopy and surgery of acromioclavicular (AC) joint.

In some embodiments, the present cannula, as attached to a surgical instrument, can be used in a lower extremity of a subject. Exemplary procedures in an lower extremity include, but are not limited to, femoral artery surgery, fascia lata release, knee lateral release, endoscopic peroneal nerve release, endoscopic leg fascial compartment release, endoscopic release of gastrocnemius, endoscopic tarsal tunnel release, endoscopic release of Morton's neuroma, endoscopic release of the plantar fascia, arthroscopy of hip, knee and ankle, subtalar joint, and endoscopic harvesting of nerve and tendon graft.

Endoscopic or arthroscopic surgical procedures that can be performed with a cannula of the present application, such as, but not limited to, a ligament or fascia release procedure, can be performed by approaching the target tissue through an incision or body opening on either the proximate or distal side of the target tissue.

In some embodiments, a cannula of the present application can be used for plastic surgery. A cannula of the present application is useful for tissue remodeling or the excision of tissue segments, including necrotic tissue.

Figure 2:
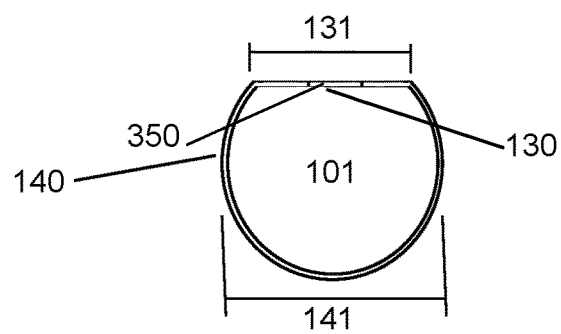
FIG. 2 shows a cross-section view of an exemplary embodiment of the present cannula (not to scale).

One aspect of the present invention relates to a cannula for a surgical instrument used for cutting selected tissue in a body cavity while under visual inspection. The cannula 100, as exemplified in FIGS. 1 & 2, comprises a hollow central lumen 101 extending from its proximal end 110 to its distal end 120; the proximal end 110 being open and connectable to a surgical handpiece, allowing passage of an optical system and a cutting tool extension system into said hollow central lumen; and said distal end 120 being closed. The cannula has a flat top surface 130 with a lateral slot 350 in the proximity of said distal end through which a cutting blade can be extended and retracted under operation of the cutting tool extension system while visualizing tissue at said lateral slot 350 with said optical system. The flat top surface 130 has a width dimension 131 spanning a distance from a first side to a second side of said flat top surface 130. The cannula 100 further has a contiguous lower surface 140 having the lateral sides thereof connected to said first side and said second side of said flat top surface, said lower surface being sized to permit a passage of an optical system and a cutting tool extension system between said flat top surface and said lower surface, said lower surface being circular in cross-section, wherein the lateral sides of said lower surface are curved such that they have a maximum width 141 between the lateral sides that is greater than said width dimension of said flat top surface.

In some embodiments, the cannula is made from a clear material. In some further embodiments, the clear material is polycarbonate. In some embodiments, the cannula is marked with gradations showing how far the cannula had been inserted through an entry portal.

In some embodiments, the hollow central lumen has a length dimension that ranges from 3 to 15 centimeters.

In some embodiments, the width dimension of said flat top surface ranges from 0.1 to 1.5 centimeters.

In some embodiments, the distal end of the cannula is turned upwards like an obturator.

Another aspect of the present application relates to a cannula for a surgical instrument used for cutting selected tissue in a body cavity while under visual inspection. The cannula comprises a hollow central lumen extending from its proximal end to its distal end; the proximal end being open and connectable to a surgical handpiece, allowing passage of an optical system and a cutting tool extension system into said hollow central lumen; and said distal end being closed. The cannula is circular in cross-section and has a lateral slot in the proximity of said distal end through which a cutting blade can be extended and retracted under operation of the cutting tool extension system while visualizing tissue at said lateral slot with said optical system.

In some embodiments, the cannula is made from a clear material. In some further embodiments, the clear material is polycarbonate. In some embodiments, the cannula is marked with gradations showing how far the cannula had been inserted through an entry portal.

In some embodiments, the hollow central lumen has a length dimension which ranges from 3 to 15 centimeters.

In some embodiments, the width dimension of said flat top surface ranges from 0.1 to 1.5 centimeters.

In some embodiments, the distal end of the cannula is turned upwards like an obturator.

In some embodiments, the cannula is removably attached to a handle capable of storing a variety of surgical or exploratory tools and selectably deploying each of those tools individually into the cannula in concert with, or attached to, a viewing device. In some embodiments, the handle comprises a rotary switch for the selection of individual tools, or for advancing the viewing device into the cannula without a tool. In some embodiments, the surgical or exploratory tools are selected from the group consisting of cutting blades, scrapers, rasps, biopsy loops and/or punches, cauteries, probes, lights and combinations thereof. In some embodiments, the handle further comprises an inner sleeve that encircles the path of the viewing device. The inner sleeve works in concert with the rotary switch and comprises notches for the storage of each individual tool.

An exemplary handle may be cylindrical, rectangular, oval or elliptical in cross-section and comprised of two halves. The proximal end of the cannula is adapted to engage with a connection point on the front end of the handle. In some embodiments, the proximal end of the cannula comprises depressions that engage with tabs (or pins) at the connection point on the front end of the handle. As used herein, the term "depression" is understood to include, but is not limited to, depressions that do not penetrate completely through the material of the cannula, as well as holes or slots that penetrate completely through the material of the cannula.

The handle further includes an opening that can be located in either half of the handle. In some embodiments, the opening may span the junction between the halves of the handle, being located partially in each half. The opening is located adjacent to an internal revolver that comprises a selector switch that protrudes through the opening.

The handle further comprises an inner sleeve that encircles a guidance tube or tube assembly. In some embodiments, the handle further comprises a slide lock. In some embodiments, the slide lock comprises notches and a tub separating the notches at its distal end that provide pre-deployment resting places for surgical or exploratory tools. The slide lock works in concert with the revolver in order to bring a surgical or exploratory tools, such as a blade or scraper, into the proper orientation for deployment into the cannula. The tube assembly provides a path for deploying an viewing device through the device and into the cannula. The tube assembly also provides, at its distal end, a mounting point or tube locator that the surgical or exploratory tool is rotated onto for deployment. At the proximate end of the handle, the tube assembly passes through a stabilizer ring, which mounts into, and seals, the proximate end of the handle. The tube assembly is advanced along the deployed viewing device into the cannula, thereby deploying the surgical or exploratory tool into the cannula.

In some embodiments, the surgical or exploratory tool, such as a blade, comprises a base that allows the tool to be secure in its pre-deployment notch of the slide lock. When the tool is rotated into deployment orientation, the notch in the base engages a mounting point on the distal end of a guidance tube or directly on the viewing device. In some embodiments, to prevent any unwanted side-to-side motion of the tool as it is deployed distally through the slot of the cannula, the tool may further comprise a ridge that fills the slot side-to-side. Additionally, the engagement of the notch with the mounting point allows the tool to be safely retracted back into the handle following usage of the tool for a surgical or exploratory procedure.

Described here is an exemplary relationship of the inner sleeve to the revolver of the device. The inner sleeve extends into the revolver and the pre-deployment slots holding the surgical or exploratory tools are located inside the revolver. In an exemplary configuration, springs are attached to pins located on the revolver. The springs extend to pins that secure the opposite end of the springs to the inner sleeve. The springs auto center the revolver within the handle. Upon rotation of the revolver, the springs activate detents for either deployment of the viewing device alone or orientation of a surgical or exploratory tool in deployment configuration.

In some embodiments, the surgical or exploratory tools are parked in notches in the inner sleeve and are retained there when not deployed by a rotary clip. The handle may further incorporate a tube assembly that passes through the inner sleeve within the handle. The distal end of the tube assembly extends and is deployable into the cannula. The tube assembly comprises near its distal end a tube locator that the surgical or exploratory tool is engaged with for deployment into the cannula. The tube assembly may further comprise, at its proximate end, a tube stop that prevents the proximate end of the tube assembly from passing through the rear of the handle. The tube assembly has a longitudinal central lumen that accommodates the insertion of a viewing device through the tube assembly and into the cannula in order to visualize the tissue surrounding said cannula and to observe the surgical procedure performed with the surgical instrument. In some embodiments, the proximal end of the tube assembly is gripped by the practitioner or engaged to a grippable attachment to allow the tube assembly to be operated manually for advancement or withdrawal of the tube assembly through the handle and cannula. In other embodiments, the proximal end of the tube assembly is engaged to an apparatus or machine for automatic or remote control of advancement or withdrawal of the tube assembly.

In some embodiments, the cannula is laterally expandable, allowing for improved stretching or separation of tissues surrounding the cannula.

In some embodiments, the cannula may further comprise one or more wings, flanges or tabs mounted at or proximal to the proximate end of the cannula. Wings, flanges or tabs may be useful for manual manipulation of the cannula addition to, or in lieu of, a handle. In some embodiments, the wings, flanges or tabs may be useful for mounting an additional surgical instrument for a procedure or for mounting the cannula to an immobilizing platform, for example for additional stability of the surgical instrument during a procedure in need thereof.

It is understood that the individual elements of the cannula and handle are not limited to the exact configuration described herein. Any design of particular elements of the cannula and handle that can be envisioned by one of ordinary skill in the art to perform the same function in concert with other elements is included as part of the present disclosure.

Another aspect of the present application relates to a method for performing a uniportal procedure with a cannula for a surgical instrument used for cutting selected tissue in a body cavity while under visual inspection. The cannula comprises a hollow central lumen extending from its proximal end to its distal end; the proximal end being open and connectable to a surgical handpiece, allowing passage of an optical system and a cutting tool extension system into said hollow central lumen; and said distal end being closed. The cannula has a flat top surface with a lateral slot in the proximity of said distal end through which a cutting blade can be extended and retracted under operation of the cutting tool extension system while visualizing tissue at said lateral slot with said optical system. The flat top surface has a width dimension spanning a distance from a first side to a second side of said flat top surface. The cannula further has a contiguous lower surface having the lateral sides thereof connected to said first side and said second side of said flat top surface, said lower surface being sized to permit a passage of an optical system and a cutting tool extension system between said flat top surface and said lower surface, said lower surface being circular in cross-section, wherein the lateral sides of said lower surface are curved such that they have a maximum width between the lateral sides that is greater than said width dimension of said flat top surface. The method comprising the steps of: a) establishing an entry portal; b) inserting the distal end of the cannula through the entry portal; c) advancing the cannula to create a passage to the target tissue; d) imaging the target tissue with the optical system; e) performing an endoscopic operation at the target tissue; and f) withdrawing the cannula from the entry portal.

In some embodiments, the cannula can be used on any target tissue, bone, joint or target area of the body of a subject.

In some embodiments, the procedure is a surgical operation comprising the steps of contacting the target tissue with a blade and dividing the target tissue with the blade. In some further embodiments, the surgical operation is carpal tunnel release and the target tissue is the transverse carpal ligament. In other further embodiments, the surgical operation is trigger finger release and the target tissue is the A1 pulley. In still other further embodiments, the surgical operation is fascia release.

Another aspect of the present application relates to a method for performing uniportal endoscopic carpal tunnel release with a cannula for a surgical instrument used for cutting selected tissue in a body cavity while under visual inspection. The cannula comprises a hollow central lumen extending from its proximal end to its distal end; the proximal end being open and connectable to a surgical handpiece, allowing passage of an optical system and a cutting tool extension system into said hollow central lumen; and said distal end being closed. The cannula has a flat top surface with a lateral slot in the proximity of said distal end through which a cutting blade can be extended and retracted under operation of the cutting tool extension system while visualizing tissue at said lateral slot with said optical system. The flat top surface has a width dimension spanning a distance from a first side to a second side of said flat top surface. The cannula further has a contiguous lower surface having the lateral sides thereof connected to said first side and said second side of said flat top surface, said lower surface being sized to permit a passage of an optical system and a cutting tool extension system between said flat top surface and said lower surface, said lower surface being circular in cross-section, wherein the lateral sides of said lower surface are curved such that they have a maximum width between the lateral sides that is greater than said width dimension of said flat top surface. The method comprising the steps of: a) establishing an entry portal proximal or distal of, and proximate to, the transverse carpal ligament; b) inserting the distal end of the cannula through the entry portal; c) advancing the cannula to create a passage to and under the transverse carpal ligament; d) imaging the transverse carpal ligament and tissues surrounding the cannula with the optical system; e) dividing the transverse carpal ligament; and f) withdrawing the cannula from the entry portal.

Kit

Another aspect of the present application relates to an instrument kit for implementing an endoscopic or arthroscopic surgical procedure. The kit comprises the cannula of the present application.

In some embodiments, the instrument kit comprises a surgical handpiece attachable to the proximal end of the cannula.

In some embodiments, the instrument kit comprises additional components and implements useful for endoscopic or arthroscopic procedures.

In another embodiment, the instrument kit further includes a scalpel.

In another embodiment, the instrument kit further includes at least one retractor for holding open an entry portal.

Method for Endoscopic or Arthroscopic Surgery

Another aspect of the present application relates to a method for uniportal endoscopic or arthroscopic surgery using the present cannula, as attached to a surgical instrument. Uniportal endoscopic or arthroscopic surgery allows the practitioner to visualize a target tissue and its surrounding tissues as well as perform a surgical procedure through a single entry portal. In some instances, the entry portal may be a natural opening, while in other instances the entry portal is an incision. In the case of an incision, generally only a single small incision must be made. In particular embodiments, the incision is less than or equal to about 2 cm in length. In more particular embodiments, the incision is less than or equal to about 1.5 cm in length. In still more particular embodiments, the incision is less than or equal to about 1 cm in length. The single small incision allows the patient to recover more quickly and begin therapy and/or resume normal activity as tolerated sooner. In some embodiments, the procedure can be a uniportal percutaneous endoscopic surgical procedure.

The uniportal endoscopic surgical procedure described herein can be used to implement a number of different surgical procedures including, but not limited to, carpal tunnel release, Guyon's canal release, cubital tunnel release, plantar fascia release, lateral release for patella realignment, release of radial tunnel, release of pronatar *teres*, release of trigger finger, release of lacertus fibrosus, release of the extensor tendons for lateral epicondylitis, release of medial epicondylitis, release of the posterior and other compartments of the leg, forearm fascia release for fascial compartment syndrome, release of fascial compartments in the upper or lower extremities, relieving the compression of a nerve by a ligament pulley or tunnel, releasing the travel of a ligament through a ligament pulley or tunnel, surgical procedures on the spine, such as endoscopic discectomy for the treatment of degenerative disc disease, herniated discs, bulging discs, pinched nerves or sciatica, endoscopic procedures on cranial and facial tissues, fasciotomy release and blood vessel harvesting.

One embodiment of the present application relates to a method for a performing a uniportal endoscopic or arthroscopic surgical procedure a target tissue in a subject. Generally, the surgical procedure requires the establishment of an entry portal. In some embodiments of the present application, the entry portal is established to the proximate side of the target tissue. In other embodiments of the present application, the entry portal is established to the distal side of the target tissue.

In some embodiments, the establishing an entry portal comprises making an incision.

In some embodiments, following the establishment of an entry portal, the distal end of the cannula is inserted through the portal to establish an opening in the underlying tissue between the portal and the target tissue. In some embodiments, the distal end of the cannula comprises a front edge for separating tissues.

The optical system is advanced from the surgical handpiece through the open proximal end of the cannula and into the hollow central lumen of the cannula to view the target tissue and the surrounding tissues, assuring that the slot of the cannula is in proper orientation to the target tissue. In some embodiments, the optical system is an endoscope or arthroscope.

In one embodiment, the surgical procedure is carpal tunnel release. In a further embodiment, the target tissue is the transverse carpal ligament.

In another particular embodiment, the surgical procedure is trigger finger release. In another particular embodiment, the target tissue is the A1 pulley.

The present invention is further illustrated by the following examples which should not be construed as limiting. The contents of all references, patents and published patent applications cited throughout this application, as well as the Figures and Tables, are incorporated herein by reference.

Example 1: Uniportal Endoscopic Carpal Tunnel Release

In a patient presenting with carpal tunnel syndrome, an incision is made just proximal or distal to the transverse carpal ligament (TCL), making an entry portal.

The distal end of the cannula, as attached to a surgical instrument, is inserted into entry portal and the front edge of the cannula is introduced into the incision and used to create a plane under the carpal transverse ligament, but superficial to the median nerve, with the slot of the cannula facing the TCL. The procedure is observed with the optical system.

The optical system is moved/rotated within the cannula to observe and image the target tissue and surrounding tissues.

Following the creation of the plane, the optical system is used to visualize the TCL. The slot of the cannula is aligned facing the TCL and positioned so that the blade, when extended from the slot, contacts the far margin of the TCL, i.e., the distal margin of the TCL when the entry portal was made proximal to the TCL, or the proximal margin of the TCL when the entry portal was made distal to the TCL.

The blade is then extended through the slot and cutting edge of the blade is moved into contact with the far margin of the TCL and the TCL is divided by withdrawing the cannula towards the entry portal, thereby drawing the cutting edge of the blade through the TCL. The blade is retracted back into the cannula when the near margin of the TCL has been reached and severed.

The cannula is then moved back towards the far margin of the TCL and the optical system is used to visualize the cut edges of the TCL. If strands of the TCL remain uncut, the blade can then be extended out from the slot again to sever those strands.

The integrity of the underlying median nerve and tendons attached to the digits are also visualized. While visualizing the nerve and tendons, release is confirmed by passive manipulation of the digits through their range of motion.

The cannula is withdrawn and removed from the entry portal. The cannula is detached from the surgical instrument and properly discarded as medical waste.

The wound is closed and a soft bandage is applied. In some cases, a splint is also applied to immobilize the wrist up to a week.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the components and steps in any sequence which is effective to meet the objectives there intended, unless the context specifically indicates the contrary.

What is claimed is:

1. A cannula for a surgical instrument used for cutting selected tissue in a body cavity while under visual inspection, said cannula comprising:
    a hollow central lumen extending from its proximal end to its distal end;
    said proximal end being open and connectable to a surgical handpiece, allowing passage of an optical system and a cutting tool extension system into said hollow central lumen; and
    said distal end being closed;
    said cannula has a flat top surface, being circular in cross-section and having a lateral slot in the proximity of said distal end through which a cutting blade can be extended and retracted under operation of the cutting tool extension system while visualizing tissue at said lateral slot with said optical system.

2. The cannula of claim 1, wherein said cannula is made from a clear material.

3. The cannula of claim 2, wherein said clear material is polycarbonate.

4. The cannula of claim 1, wherein said hollow length has a length dimension which ranges from 3 to 15 centimeters.

5. The cannula of claim 1, wherein the flat top surface has a width and dimension spanning a distance from a first side to a second side of the flat top surface, wherein said width dimension of said flat top surface ranges from .1 to 1.5 centimeters.

6. The cannula of claim 1, wherein said distal end is turned upwards like an obturator.

7. The cannula of claim 1, wherein said distal end of the cannula comprises a front edge for separating tissues.

8. A method for performing a uniportal procedure with the cannula of claim 1 for a surgical instrument used for cutting selected tissue in a body cavity while under visual inspection the method comprising the steps of:
   a) establishing an entry portal;
   b) inserting the distal end of the cannula through the entry portal;
   c) advancing the cannula to create a passage to a target tissue;
   d) imaging the target tissue with the optical system;
   e) performing an endoscopic operation at the target tissue; and
   f) withdrawing the cannula from the entry portal.

9. The method of claim 8, wherein the target tissue is bone or joint.

10. The method of claim 8, wherein said procedure is a surgical operation comprising the steps of contacting the target tissue with a blade and dividing the target tissue with the blade.

11. The method of claim 9, wherein said surgical operation is carpal tunnel release and the target tissue is the transverse carpal ligament.

12. The method of claim 9, wherein said surgical operation is trigger finger release and the target tissue is the A1 pulley.

13. The method of claim 9, wherein said surgical operation is fascia release.

14. A method for performing uniportal endoscopic carpal tunnel release with the cannula of claim 1 for a surgical instrument used for cutting selected tissue in a body cavity while under visual inspection, the method comprising the steps of:
   a) establishing an entry portal proximal or distal of, and proximate to, a transverse carpal ligament;
   b) inserting the distal end of the cannula through the entry portal;
   c) advancing the cannula to create a passage to and under the transverse carpal ligament;
   d) imaging the transverse carpal ligament and tissues surrounding the cannula with the optical system;
   e) dividing the transverse carpal ligament; and
   f) withdrawing the cannula from the entry portal.

* * * * *